(12) United States Patent
Meyer

(10) Patent No.: US 7,150,719 B2
(45) Date of Patent: Dec. 19, 2006

(54) THORACO-LUMBAR SPINE SUPPORT/BRACE

(76) Inventor: Donald W. Meyer, 18042 Magnolia St., Fountain Valley, CA (US) 92708

( * ) Notice: Subject to any disclaimer, the term of this patent is extended or adjusted under 35 U.S.C. 154(b) by 511 days.

(21) Appl. No.: 10/756,929

(22) Filed: Jan. 14, 2004

(65) Prior Publication Data

US 2005/0154337 A1    Jul. 14, 2005

(51) Int. Cl.
*A61H 1/00* (2006.01)
(52) U.S. Cl. .............................. 601/19; 601/5; 482/148
(58) Field of Classification Search ............... 602/5, 602/19, 32–35, 38; D24/190; 128/96.1, 128/98.1, 99.1, 105.1, 845, 846; 482/69, 482/124, 148
See application file for complete search history.

(56) References Cited

U.S. PATENT DOCUMENTS

| | | | | |
|---|---|---|---|---|
| 2,835,247 A | * | 5/1958 | Stabholc | 602/19 |
| 2,886,031 A | * | 5/1959 | Robbins | 602/19 |
| 3,029,810 A | * | 4/1962 | Martin | 602/19 |
| 3,220,407 A | * | 11/1965 | Connelly | 602/19 |
| 4,715,362 A | * | 12/1987 | Scott | 602/36 |
| 4,987,885 A | * | 1/1991 | Shtabholz | 606/241 |
| 6,210,354 B1 | * | 4/2001 | Ousdal | 602/36 |
| 6,280,405 B1 | * | 8/2001 | Broselid | 602/36 |

OTHER PUBLICATIONS

Website page: www.idealspine.com/Advertisers/standingtxn/all_new_standing_sagittal_tracti; "All New Standing Sagittal Traction"; printed Apr. 26, 2004, 1 page.
Website page: www.promotechiropractic.com/Pages/home; "What is the Regainer System?"; printed Apr. 26, 2004; 2 pages.
Harrison, Deed E., et al.; "How do anterior/posterior translations of the thoracic cage affect the sagittal lumbar spine, pelvic tilt, and thoracic kyphosis?" Abstract; Eur. Spine; Jan. 2002; 11: 287-293.

* cited by examiner

*Primary Examiner*—Stephen R. Crow
*Assistant Examiner*—Allana Lewin
(74) *Attorney, Agent, or Firm*—Stetina Brunda Garred & Brucker

(57) ABSTRACT

A thoraco-lumbar spine support/brace for correcting lateral spinal alignment. The brace comprises a frame member defined by two elongate bracing rods extending vertically in generally parallel relation to one another on opposed sides of the body of the wearer that extend generally from the wearer's shoulders to pelvis. Extending across the upper-most ends of the bracing rods is a posterior traction belt. At least two anterior traction slings are provided that extend across an intermediate portion of the bracing rods. A pelvic arch is further provided that extends across the bottom-most ends of the opposed bracing rod members. The posterior traction belt, anterior traction slings and pelvic arch may all be selectively positioned to impart a desired physiological orientation of the waerer's spine, and can be utilized to treat a given condition such as abnormal thoracic kyphosis, pelvic inclination and lumbar lordosis.

9 Claims, 4 Drawing Sheets

THORACO-LUMBAR SPINE SUPPORT/BRACE

CROSS-REFERENCE TO RELATED APPLICATIONS

Not Applicable

STATEMENT RE: FEDERALLY SPONSORED RESEARCH/DEVELOPMENT

Not Applicable

BACKGROUND OF THE INVENTION

Systems and devices for correcting abnormal lateral spinal curvature are well-known in the art. Typically, such devices are operative to selectively impart one or more traction forces about a patient's spinal column, usually about the cervical, thoracic and lumbar vertebrae. In this regard, it is well-documented that the selective application of such forces is operative to treat a number of conditions associated with abnormal curvature of the spine, including kyphosis and lordosis. Such traction is further operative to treat pelvic inclination abnormalities that result from the presence of excessively obtuse or acute sacral angle, which is typically recognized in the art as either above or below thirty-nine degrees, and associated with posterior and anterior thoracic translation posture.

Exemplary of such prior art systems include the Standing Sagittal Traction Unit, produced by Chiropractic Biophysics of Evanston, Wyo., which is designed for thoraco-lumbar pelvic spinal correction, and the Regainer 2000 System, produced by Promote Chiropractic of Saugus, Mass., which is operative to impart a compression/extension traction method about the full length of the spine. In this regard, such systems are operative to impart correction forces about the spinal column while the patient maintains a static posture, such as in a recumbent, inclined or seated position.

Despite the effectiveness of such systems to effectuate and accurately apply traction forces to attempt to correct abnormal lateral spinal curvature, such systems have limited effectiveness and suffer from numerous drawbacks. Perhaps the most significant of such drawbacks is that such systems are operative to apply traction forces while the patient remains in a static position. In this regard, clinical data suggests that the static application of traction forces has limited ability to change lateral spine curvature (i.e., curvature of the spine along a sagittal axis), and that when so applied a patient's muscles tend to tighten up to guard or protect the area about which the traction force is applied. Moreover, clinical data tends to suggest that the application of traction forces is less effective when applied to static or slow moving spinal tissues, which occurs when a patient assumes an immobilized position; however, most patients typically must remain immobilized when utilizing prior art systems, such as those discussed above.

In addition to their suboptimal effectiveness, it is also well-known that prior art traction systems typically possess complex, oversized structures having an excessive amount of bulky equipment, such as traction cords, weights, pulleys and the like, that are space inefficient and difficult to operate. Moreover, such systems are well-known to be quite costly, expensive to maintain, and typically can only be utilized in a specialized facility, such as a physical rehabilitation center, doctor's office or the like. As a consequence, the use of such prior art systems is not only expensive to utilize, but often times quite difficult for patients to access.

Accordingly, there is a substantial need in the art for a device, and more particularly a thoraco-lumbar spine support/brace that is operative to selectively impart a plurality of traction forces, and preferably translational forces about the spinal column and pelvis along a sagittal axis that is substantially more comfortable, efficient and effective than prior art systems, such as those discussed above. There is likewise a need in the art for such support/brace that, by virtue of being capable of applying an effective amount of traction forces to select target areas about the spinal column and pelvis, is able to treat a wide variety of conditions involving abnormal spinal curvature, including but not limited to thoracic kyphosis, lumbar lordosis and pelvic inclination, among many others. Still further, there is a need in the art for such a support/brace that is of exceedingly simple construction, space efficient, substantially less expensive than prior art systems, is portable, and capable of being utilized in environments other than physical rehabilitation centers, doctor's offices and the like. Still further, and perhaps most importantly, there is a need for such a spinal support/brace that is operative to impart corrective translational forces about the spinal cord and pelvis of an individual that further simultaneously allows for patient mobility to thus enable a synergistic effect to occur between the concurrent application of corrective spinal positioning, as accomplished by the application of precise traction forces, coupled with ambulatory treatment.

BRIEF SUMMARY OF THE INVENTION

The present invention specifically addresses and alleviates the above-identified deficiencies in the art. In this regard, the present invention is directed to a portable, lightweight thoraco-lumbar spine support/brace that is operative to correct lateral spine alignment so that the same attains a desired physiological orientation. The spine support/brace of the present invention is further operative to be worn in a variety of configurations to thus treat a wide variety of conditions, including but not limited to abnormal thoracic kyphosis, pelvic inclination and lumbar lordosis and further advantageously enables the patient to be mobile, to thus allow walking and other physical activity, while the same is worn.

According to a preferred embodiment, the spine support/brace of the present invention comprises a frame defined by a pair of elongate bracing rods or frame members having upper and lower ends that extend vertically in generally parallel relation to one another upon opposed sides of the wearer's body from the wearer's shoulders to the wearer's pelvis. Extending across the top most ends of the frame members is a posterior traction belt that, depending upon the particular condition sought to be treated or physiological orientation sought to be attained, may be positioned upon the frame members such that the same either: 1) is secured across the anterior shoulders of the wearer; 2) is secured across the upper chest and under the arms of the wearer; or 3) secured under the chest of the wearer. The support/brace further comprises at least two, and preferably between two to four anterior traction slings that are extensible across the bracing rods or frame members and positionable against the wearer's back at select positions thereof. In this regard, the anterior traction slings, as per the posterior traction belt, may be selectively positioned to treat a given condition or attain a desired physiological orientation. Such slings will extend across the bracing rods in generally horizontal parallel relation to one another and may be positioned such that: 1) a first or upper anterior traction sling extends across and compresses against the mid thoracic region and a second inferior or lower traction sling extending across and compresses against the upper lumbar region; 2) both the superior and inferior traction slings extend across and compress against the lumbosacral/pelvic ilium regions of the wearer's back; 3) both the superior and inferior traction slings extend across and compress against the mid-thoracic region of the wearer's back; and 4) the superior sling extends across and compresses against the upper lumbar region and the inferior sling extends across and compresses against the lower lumbar region. The support/brace further includes a pelvic arch that extends across the lower most ends of the bracing rods/frame members and, too, may be adjusted to impart a desired traction force to the wearer. Specifically, the pelvic arch is operatively positionable to assume: 1) a first configuration whereby the pelvic arch extends across and compresses against the superior bony structures of the ilium of the wearer; and 2) a second configuration whereby the pelvic arch extends downwardly and compresses against the anterior section in front of the wearer's hip joints. With respect to the positioning of the pelvic arch member, the bracing rods of the spine support/brace of the present invention may be selectively lengthened or shortened to thus enable the pelvic arch to be accurately positioned and impart the desired support at the aforementioned regions.

The ability to manipulate the various placement of the posterior traction belt, anterior traction slings and pelvic arch advantageously enables the spine support/brace of the present invention to selectively impart horizontal anterior or posterior support about a sagittal axis extending about the pelvis and spinal column of the wearer. Moreover, the spine support/brace of the present invention is specifically configured to impart such collective translational forces while enabling the wearer to be mobile. In this regard, the support/brace of the present invention enables a synergistic effect to take place whereby not only are corrective translational forces selectively applied about the spine and pelvis of the wearer, but by further enabling the wearer to be mobile, in sharp contrast to most prior art support/traction devices that immobilize the patient to be treated, the support/brace of the present invention advantageously provides for ambulatory treatment, namely, enabling the wearer to be mobile while normal lateral spinal alignment is in traction and held in place. In this regard, the support/brace of the present invention advantageously imparts normal lateral spinal alignment coupled with the ambulatory effect imparted by patient mobility, which has been advantageously discovered to enable spinal tissues to undergo rapid movement and thus elongate and remodel faster than static or slow moving spinal tissues that lay dormant via the use of non-ambulatory prior art traction machines.

The support/brace of the present invention may be fabricated form any of a variety of well-known materials in the art, and is preferably constructed to be of light weight, durable construction and operative to achieve the dual goals of being comfortable to wear, but at the same time imparting a desired degree of support or traction to thus ensure normal lateral spinal alignment. Also, it is imperative that the posterior traction belt, anterior traction slings, and pelvic arch be expressly configured to impart a cooperative effect and thus impart the appropriate translational forces to thus treat a given condition. Advantageously, by providing such cooperative effect, the support/brace of the present invention is operative to treat a wide variety of abnormal spinal conditions, including decreased or increased thoracic kyphosis, pelvic inclination and lumbar lordosis.

BRIEF DESCRIPTION OF THE DRAWINGS

These as well as other features of the present invention will become more apparent upon reference to the drawings.

DETAILED DESCRIPTION OF THE INVENTION

The detailed description set forth below is intended as a description of the presently preferred embodiment of the invention, and is not intended to represent the only form in which the present invention may be constructed or utilized. The description sets forth the functions and sequences of steps for constructing and operating the invention. It is to be understood, however, that the same or equivalent functions and sequences may be accomplished by different embodiments and that they are also intended to be encompassed within the scope of the invention.

Figure 1:
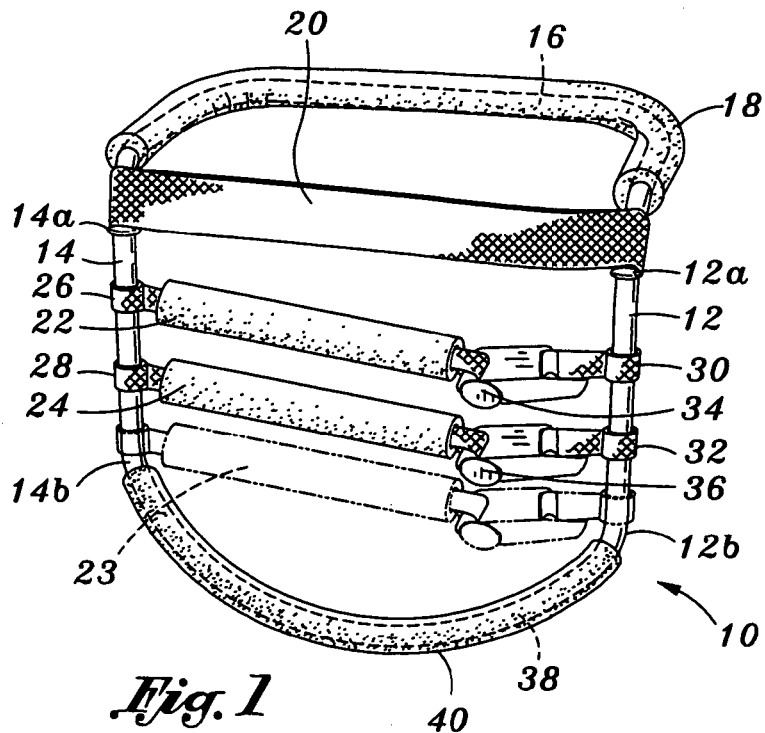
FIG. 1 is a frontal perspective view of a thoraco-lumbar spine support/brace as constructed in accordance with a preferred embodiment of the present invention.

Referring now to the Figures, initially to FIG. 1, there is shown a thoraco-lumbar spine support/brace 10 that is operative to correct lateral spinal alignment so that the same attains a desired physiological orientation. The support/brace 10 is further specifically configured to selectively apply translational traction forces at select portions upon a wearer's thoracic and lumbar vertebrae, as well as to selectively apply force upon the sacral vertebrae in order to properly maintain the sacral angle in a normal physiological orientation.

To achieve that end, the support/brace 10 comprises first and second elongate bracing rods of frame members 12,14 that each have upper end portions 12a, 14a and lower end portions 12b,14b. As illustrated, the bracing rods 12, 14 are preferably configured to extend in a generally vertical, parallel relation to one another.

Extending across and joining the top ends 12a,14a of bracing rods 12,14 is a generally "U" shaped member 18 that is provided to impart structural stability of the support/brace 10 and is configured to accommodate and extend about the wearer's uppermost shoulders and around the cervical vertebrae. Although not intended to impart any type of anatomical support, member 18 will preferably be provided with padding 16 to provide comfort to the patient. Along these lines, bar 18 along with padding 16 are operative to provide structural rigidity and to adapt the support/brace 10 to human anatomical considerations.

Also extending across the upper most ends 12a,14a of bracing rods 12,14 is a posterior traction belt 20, which is operative to selectively impart a traction force about the anterior shoulders and chest of the wearer, as discussed more fully below. As will be appreciated by those skilled in the art, the posterior traction belt 20 may be fabricated from a variety of materials that are durable in nature and capable of imparting a very strong traction force that can be selectively adjusted. Exemplary of such materials capable of being utilized in the construction of the posterior traction belt include nylon, leather, and other like materials that can be selectively adjusted through any of a variety of means well known in the art, such as by hook/loop fasteners, belts mechanisms, and the like.

Extending across the intermediate portions of the bracing rods 12,14 are at least two, and preferably between two to four anterior traction slings 22,23 (shown in phantom),24, which comprise foam padding extending about dedicated strap members such as 26, 28. To impart a selectively adjustable traction force about various portions of the wearer's thoracic and lumbar vertebrae, each respective anterior traction sling 22,24 will be provided with a dedicated adjustment mechanism 34,36, coupled to strap portions 30,32 respectively, that may be manually adjusted to impart a desired degree of support/traction force. As per the posterior traction belt 20, anterior traction slings 22,23,24 may be fabricated from nylon strap materials with conventional padding. The adjustment mechanisms 34,36 may likewise take any of a variety of tension setting mechanisms known in the art, such as ratchet wrench straps, notched belts, hook and loop fasteners and the like.

Towards the bottom portion of the support/brace 10 is a pelvic arch defined by tubing or support member 38, the latter extending in a generally outward arcuate configuration from the bottom most ends 12b,14b of bracing rods 12,14. To provide patient comfort, it is contemplated that member 38 will be provided with padding 40.

Figure 2:
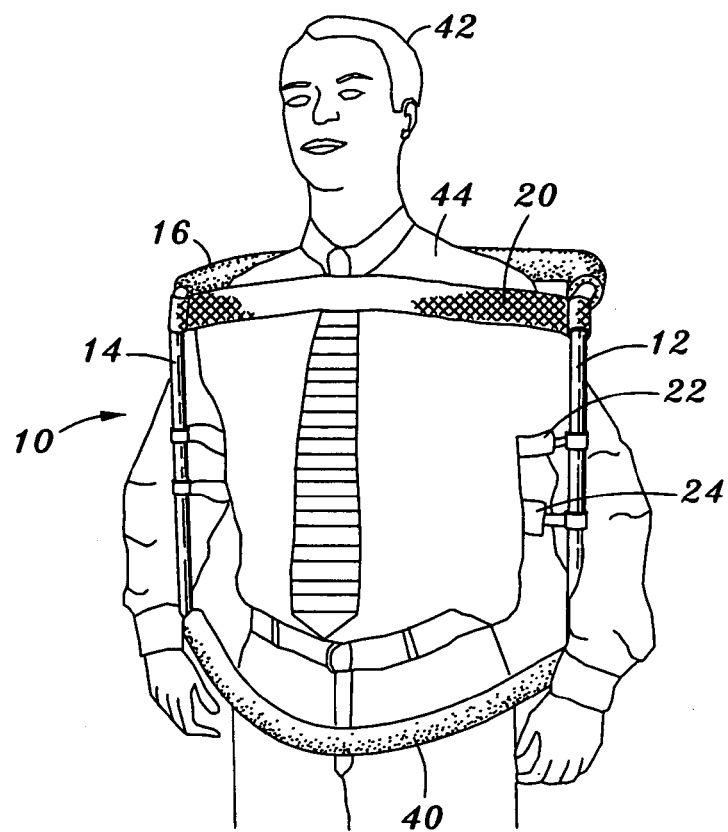
FIG. 2 is a perspective view of an individual wearing the support/brace depicted in FIG. 1.

Referring now to FIG. 2, there is shown the support/brace 10 of the present invention as worn about the chest, back and pelvis of the wearer 42. As shown, bracing rods 12,14 extend vertically on opposed sides of the wearer 42 such that foam pad 16 extends behind the wearer 42 and the posterior traction belt 20 is oriented to compress about the chest and anterior shoulders of the individual 42, the latter as shown. Likewise, the anterior traction slings 22,24 operatively extend about the back of the wearer and are likewise selectively positionable about the length of the wearer's thoracic and lumbar vertebrae. Extending across and selectively compressible against the anterior section of the wearer's pelvis is padded pelvic arch member 40, which is likewise capable of being selectively positioned to impart a specific translational force to help achieve desired positioning of the wearer's spinal column.

As will further be appreciated by reference to FIG. 2, the support/brace 10 of the present invention is capable of being worn by the wearer 42 and thus impart a variety of traction forces thereto to achieve optimal spinal positioning, while at the same time enabling the wearer 42 to be ambulatory: As illustrated, the wearer 42 is capable of assuming a standing, upright configuration and is thus capable of walking or doing other upright maneuvers. As will be appreciated by those skilled in the art, prior art traction systems require that the individual upon which the traction forces are to be applied assume a static position that does not permit any movement by the patient. The support/brace 10 of the present invention, in contrast, not only imparts the desired traction forces necessary to attain optimal spinal column positioning, but further allows for the wearer 42 to concurrently engage in physical activity, and in particular walking, which is widely recognized as an essential component of most rehabilitation regimens prescribed to treat spinal curvature abnormalities. In this regard, clinical data tends to suggest that exercise is operative to increase elasticity of spinal tissues and, when coupled with normal lateral spinal alignment, will cause spinal tissues to elongate and remodel faster.

Referring now to FIGS. 3–11, there is shown how the posterior traction belt 20, anterior traction slings 22–24 and pelvic arch, shown as element 40, may be operatively positioned in order to impart therapeutic, translational traction forces about various parts of the wearer's body, and in particular traction forces applied vertically about the wearer's spinal column and pelvis.

Figure 3:
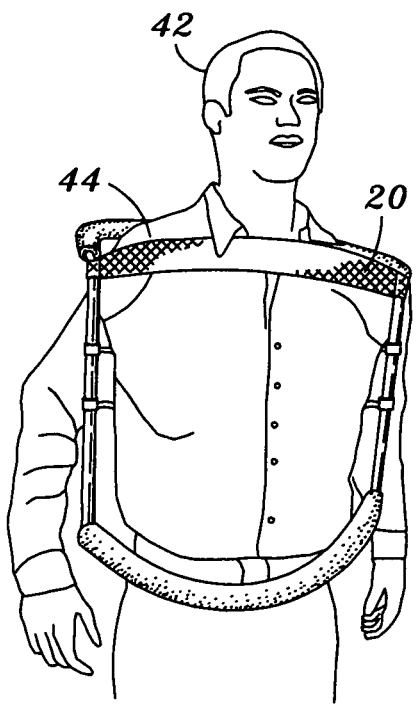
FIG. 3 is a frontal perspective view of an individual wearing the support/brace of the present invention wherein the posterior traction belt of the support/brace is shown in a first operative configuration.
Figure 4:
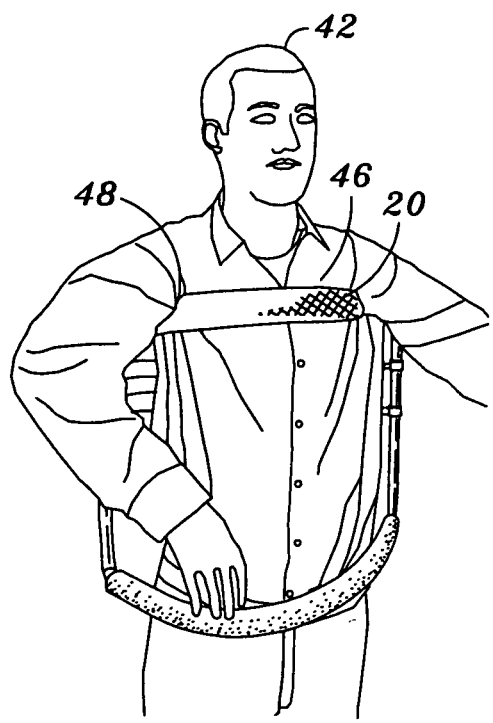
FIG. 4 is a perspective view of the individual and support/brace of FIG. 3 wherein the posterior traction belt is shown assuming a second operative configuration.
Figure 5:
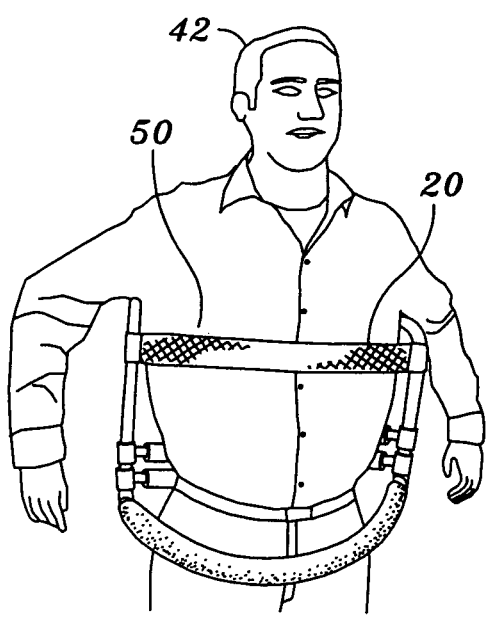
FIG. 5 is a perspective view of the individual and support/brace of FIGS. 2 and 3 wherein the posterior traction belt is shown assuming a third operative configuration.

With reference now to FIGS. 3–5, there is shown three specific configurations the posterior traction belt 20 may be operatively secured upon the wearer 42 in order to address a particular condition. As illustrated in FIG. 3, the posterior traction belt 20 extends across the anterior shoulders of the wearer 42, which should be utilized if the wearer 42 presents with forward shoulder roll, as is common with posterior thoracic translation posture. In FIG. 4, the posterior traction belt 20 is operatively positioned across the upper chest 46 and under the arms, such as 48, as will be appropriate if the patient presents with retracted shoulders, which as those skilled in the art would appreciate is common with anterior thoracic translation posture. To the extent the patient presents with neither anterior nor posterior thoracic translation posture, but rather loss of lumbar lordosis, the posterior traction belt 20 should be secured under the chest 50, as depicted in FIG. 5. As will be readily appreciated, however, the placement of posterior traction belt 20 in such manner should only be used for lumbar traction.

Figure 6:
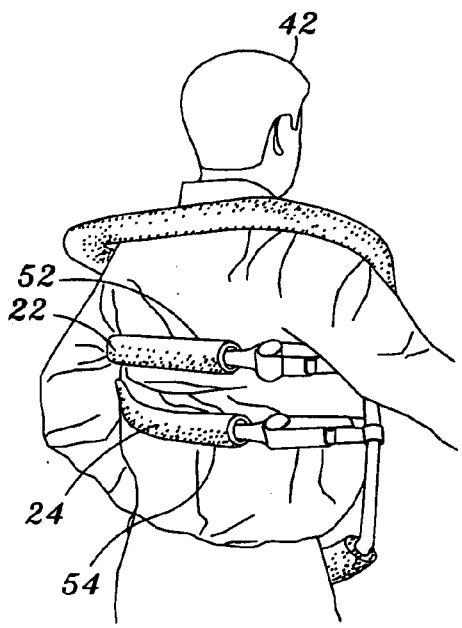
FIG. 6 is a rear perspective view of an individual wearing a support/brace of the present invention depicting two anterior traction slings, namely a superior traction sling and an inferior traction sling, shown assuming a first operative configuration.

With respect to the anterior traction slings 22,24, the same are operative to assume at least four different configurations as will be appropriate for specific types of conditions. Referring now to FIG. 6, the upper or superior sling 22 extends across and compresses against the mid-thoracic region 52 and the lower or inferior sling 24 extends across and compresses against upper lumbar region of the wearer 42. Such application is appropriate if the patient presents with an increased thoracic kyphosis, decreased upper lumbar lordosis and increase lower lumbar lordosis as is common in posterior thoracic translation posture.

Figure 7:
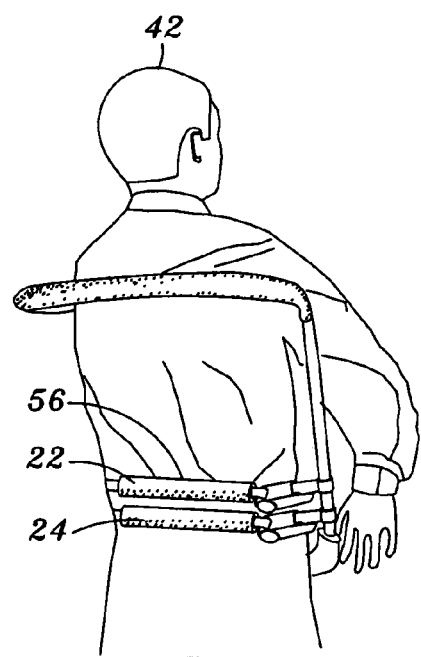
FIG. 7 is a perspective view of an individual and support/brace of FIG. 6 wherein the anterior traction slings are shown assuming a second operative configuration.

Referring now to FIG. 7, the anterior slings 22,24 are operatively configured such that both slings 22,24 extend across and compress against a lumbosacral/pelvic ilium region to thus pull the support/brace 10 of the present invention and the wearer's thorax in a posterior manner. Such configuration is appropriate in those individuals who present with a decreased thoracic kyphosis, decreased lower lumbar lordosis, and pelvic inclination.

Figure 8:
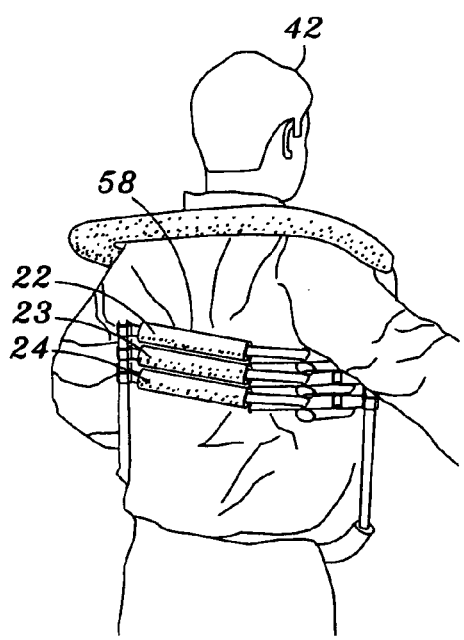
FIG. 8 is a perspective view of the individual and support/brace of FIGS. 6 and 7 wherein the anterior traction slings are shown assuming a third operative configuration.

Alternatively, to the extent the patient presents mainly increased thoracic kyphosis, the anterior slings should be tightened down across the wearer's mid-thoracic region. As illustrated in FIG. 8, there is shown the cooperative effect of three anterior slings, namely, 22,23,24, all of which are shown extending across and supporting mid-thoracic region 58.

Figure 9:
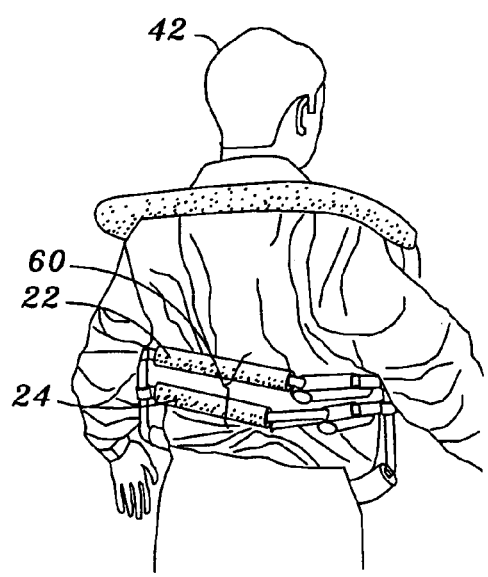
FIG. 9 is a perspective view of the individual and support/brace of FIGS. 6 and 7 wherein the anterior traction slings are shown assuming a fourth operative configuration

Referring now to FIG. 9, the anterior slings 22,24 are shown extending across and bracing the upper and lower lumbar regions 60. Such configuration is appropriate to the extent the wearer has mainly decreased lumbar lordosis. To the extent applicable, either the superior or upper sling 22 may be tightened to a greater degree to the extent the lordotic loss is more severe in the upper lumbar region or, alternatively, the inferior or lower sling 24 may be tightened to the extent lordotic loss is more severe in the lower lumbar region. The relative degree of lordotic loss may be readily determined utilizing techniques well-known in the art.

Figure 10:
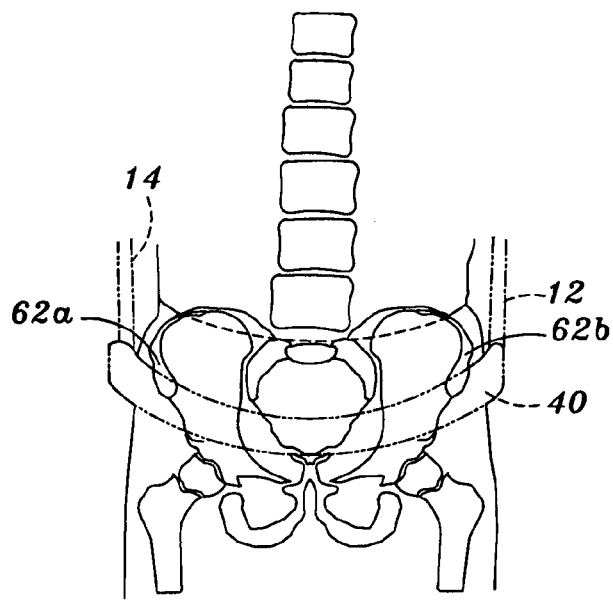
FIG. 10 is a frontal view of the skeletal structures of an individual's spinal column, pelvis and hip joints wherein it is further depicted a pelvic arch, shown in phantom, as part of the support/brace of the present invention shown extending across the anterior section of the pelvis such that the pelvic arch is aligned with the individual's superior ilium.
Figure 11:
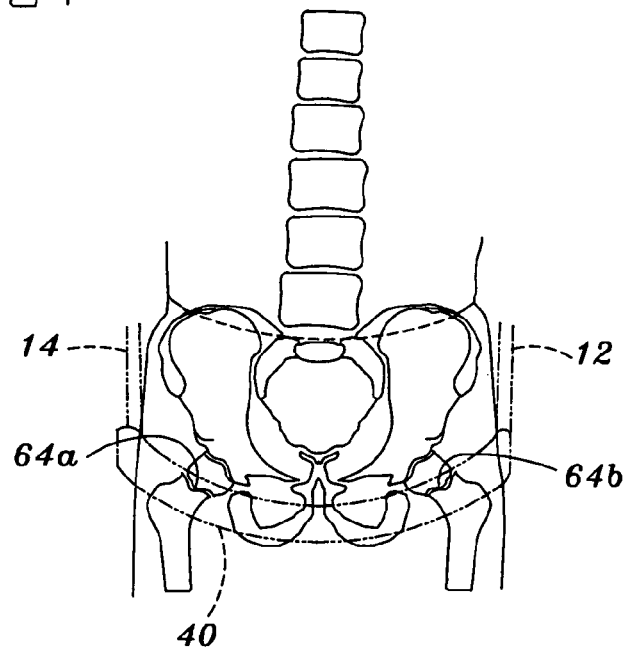
FIG. 11 is a frontal perspective view of the skeletal structures of FIG. 10 wherein the pelvic arch of the support/brace of the present invention is shown extending across the individual's hip joints.

Referring now to FIGS. 10 and 11, and initially to FIG. 10, there is shown the relative orientation of the pelvic arch member 40 of the support/brace 10 of the present invention and how the same is operative to impart a translational traction force to the anterior section of the pelvis. As illustrated, pelvic arch 40 extends across lower most portions 12b, 14b of bracing rods 12.14, and as shown in FIG. 10, extend across and compressively engage against the bony structures defining the ilium, 62, 62b of the wearer's skeletal structure. In this regard, and unlike prior art devices, the pelvic arch 40 is operative to impart the compressive force to both opposed sides of the pelvis and specifically targets the ilium 62a,62b at the point of abutment to impart the traction force. The sensitive anterior mid-line organs (i.e., bladder, intestines) are not contacted or pressured. As will be readily appreciated by those skilled in the art, the support imparted by pelvic arch 40 to the superior ilium 62a,62b of the patient is appropriate for individuals who present with a sacral angle of more than thirty-nine degrees, because it induces pelvic extension when the anterior slings are tightened.

On the other hand, to the extent the individual possesses a sacral angle of less than thirty-nine degrees, the pelvic arch 40 will be operatively adjusted to assume the configuration shown in FIG. 11. As illustrated, the pelvic arch is configured to extend across and compress against the anterior section in front of the hip joints 64a,64b of the wearer's skeletal structure. Such compressive force, in conjunction with the anterior traction sling forces, is operative to cause the sacral angle to flex to its normal physiological orientation of approximately thirty-nine degrees.

In order to attain the configurations illustrated and described with respect to FIGS. 10 and 11, it is contemplated that the pelvic arch 40, and more particularly the tubing structure 38 disposed therewithin, as depicted in FIG. 1, will be telescopically received and selectively fastenable within the opposed lower ends 12b,14b of bracing rods 12,14. Along these lines, it is contemplated that such arrangement will enable the support/brace 10 of the present invention to not only readily provide an accurately applied translational traction force that can address either abnormally obtuse or acute sacral angles, but can enable the support/brace 10 of the present invention to be readily worn by individuals of dissimilar size. In this regard, it is contemplated that by enabling the pelvic arch 40 to selectively extend from the opposed lower ends of bracing rods 12,14, the support/brace 10 of the present invention may be readily worn by virtually any size of individual, whether tall, short, male or female.

Moreover, given the space efficient nature by which all three traction force imparting mechanisms, namely, posterior traction belt, anterior slings and pelvic arch, are able to achieve their desired result, as well as the simple construction associated therewith, the support/brace 10 of the present invention is not limited per prior art systems that must remain stationary and/or otherwise possess complex structure that is costly to maintain.

Additional modifications and improvements of the present invention may also be apparent to those of ordinary skill in the art. Thus, the particular combination of parts and steps described and illustrated herein is intended to represent only certain embodiments of the present invention, and is not intended to serve as limitations of alternative devices and methods within the spirit and scope of the invention.

What is claimed is:

1. A device for supporting and bracing the thoraco-lumbar region of an individual's spine when said device is worn by said individual, said device comprising:

a. first and second elongate bracing rods having upper and lower ends and disposed in generally parallel relation to one another, said first and second bracing rods being positionable on opposed sides of said individual when said device is worn by said individual;

b. a posterior traction belt extending across said upper most ends of said bracing rods and positionable across a region of said individual's body, said region being selected from the group consisting of the individual's anterior shoulders and the individual's chest;

c. at least two anterior traction slings extending across an intermediate portion of said first and second bracing rods and operatively positionable against a region of said individual's spine, said region being selected from the group consisting of the individual's thoracic vertebrae, the individual's lumbar vertebrae and said individual's sacral vertebrae;

d. a pelvic arch affixed to and extending from the lower most ends of said first and second bracing rods and operative to be positioned against a portion of the individual's pelvic region, said region being selected from the group consisting of the anterior superior portion of said individual's ilium and the anterior section of said individual's hip joint; and e. a support bar extending from the top most ends of said first and second bracing rods, said support bar having a generally arcuate shape and operative to extend behind the shoulders and neck of said individual while such individual wears said device.

2. The device of claim 1 wherein said device further comprises a mechanism for adjusting the tension and traction force imparted by said posterior traction belt.

3. The device of claim 1 wherein said device further comprises dedicated mechanisms for adjusting the tension and traction force imparted by each respective one of said anterior traction slings.

4. The device of claim 1 wherein said device further comprises a mechanism for selectively adjusting and securing into position said pelvic arch.

5. The device of claim 4 wherein said pelvic arch is operatively coupled to said lower-most ends of said first and second bracing rods such that the height of said pelvic arch member relative the individual wearing said device may be selectively adjusted.

6. The device of claim 1 wherein said support bar is provided with foam padding.

7. The device of claim 1 wherein each respective one of said anterior traction slings is provided with foam padding.

8. The device of claim 1 wherein said pelvic arch member is provided with foam padding.

9. The device of claim 1 wherein said posterior traction belt of said device may be operatively positioned against a region of said individual wearing said device selected from the group consisting of the anterior shoulders, upper chest and below the chest.

* * * * *